United States Patent
Gupton et al.

(10) Patent No.: US 10,077,242 B2
(45) Date of Patent: Sep. 18, 2018

(54) CONVERGENT APPROACH TO THE TOTAL SYNTHESIS OF TELMISARTAN VIA A SUZUKI CROSS-COUPLING REACTION

(71) Applicant: VIRGINIA COMMONWEALTH UNIVERSITY, Richmond, VA (US)

(72) Inventors: Frank Gupton, Midlothian, VA (US); Alex Martin, Richmond, VA (US); Ali Siamaki, Richmond, VA (US); Katherine Belecki, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 15/529,615

(22) PCT Filed: Dec. 1, 2015

(86) PCT No.: PCT/US2015/063152
§ 371 (c)(1),
(2) Date: May 25, 2017

(87) PCT Pub. No.: WO2016/089845
PCT Pub. Date: Jun. 9, 2016

(65) Prior Publication Data
US 2017/0260146 A1 Sep. 14, 2017

Related U.S. Application Data

(60) Provisional application No. 62/085,842, filed on Dec. 1, 2014, provisional application No. 62/088,198, filed on Dec. 5, 2014.

(51) Int. Cl.
| | | |
|---|---|---|
| *C07D 235/20* | (2006.01) | |
| *C07D 403/04* | (2006.01) | |
| *B01J 23/44* | (2006.01) | |
| *B01J 21/18* | (2006.01) | |
| *B01J 31/22* | (2006.01) | |
| *B01J 31/24* | (2006.01) | |
| *B01J 35/00* | (2006.01) | |

(52) U.S. Cl.
CPC ............ *C07D 235/20* (2013.01); *B01J 21/18* (2013.01); *B01J 23/44* (2013.01); *B01J 31/2295* (2013.01); *B01J 31/2409* (2013.01); *B01J 35/0006* (2013.01); *C07D 403/04* (2013.01); *B01J 2231/4211* (2013.01); *B01J 2531/824* (2013.01); *B01J 2531/842* (2013.01)

(58) Field of Classification Search
CPC ........................... C07D 235/20; C07D 403/04
See application file for complete search history.

(56) References Cited

U.S. PATENT DOCUMENTS

| 6,455,507 B1 * | 9/2002 | Drach ................. C07D 235/24 514/248 |
|---|---|---|
| 2006/0094883 A1 | 5/2006 | Perlman et al. |

FOREIGN PATENT DOCUMENTS

CN 102050791 A 5/2011

OTHER PUBLICATIONS

Favretto, L. Basic Guidelines for Microwave Organic Chemistry Applications, Milestone Srl., 2004, pp. 1-42.*
Kawasaki et al. Heterocycles 1996, 43, 1375-1379.*
Neochoritis et al., "Convenient synthesis of polybrominated imidazole building blocks", Arkivoc, 2007, pp. 101-111, vol. xv.
Lewis et al., "Direct Functionalization of Nitrogen Heterocycles via Rh-Catalyzed C—H Bond Activation", Acc. Chem. Rest, Aug. 2008, pp. 1013-1025, vol. 41, No. 8.
Kapp, Co. "Microwave dielectric heating in synthetic organic chemistry", Chem. Soc. Rev., 2008, pp. 1127-1139, vol. 37.
Goossen et al., "Concise Synthesis of Telmisartan via Decarboxylative Cross-Coupling", J. Org. Chem., 2008, pp. 8631-8634, vol. 73.
Martin et al., "A Convergent Approach to the Total Synthesis of Telmisartan via a Suzuki Cross-Coupling Reaction between Two Functionalized Benzimidazoles", J. Org. Chem., 2015, pp. 1915-1919, vol. 80.

* cited by examiner

*Primary Examiner* — Matthew P Coughlin
(74) *Attorney, Agent, or Firm* — W&C IP

(57) ABSTRACT

Methods of synthesizing the angiotensin II receptor antagonist telmisartan in high yield and purity are provided. The methods involve the coupling of two structurally distinct benzimidazole units via a Suzuki cross-coupling reaction. Methods of regioselectively synthesizing one of the benzimidazole units are also provided.

18 Claims, No Drawings

CONVERGENT APPROACH TO THE TOTAL SYNTHESIS OF TELMISARTAN VIA A SUZUKI CROSS-COUPLING REACTION

CROSS-REFERENCE TO RELATED APPLICATIONS

This application claims benefit of U.S. provisional patent applications 62/085,842, filed Dec. 1, 2014 and 62/088,198, filed Dec. 5, 2014, the complete contents of both of which are hereby incorporated by reference.

BACKGROUND OF THE INVENTION

Field of the Invention

The invention generally relates to improved methods of synthesizing the angiotensin II receptor antagonist telmisartan. In particular, the invention provides methods which involve a Suzuki cross-coupling of two structurally distinct benzimidazole units, one of which may be formed using a novel method of regioselective bromination.

Background

Telmisartan (1) is a potent angiotensin II receptor antagonist used in the treatment of essential hypertension.[1-3] It is one of the most efficacious drugs in its class, boasting the longest half-life, a high protein binding affinity and a low daily dosage.[4,5] The drug is currently marketed under the brand name of Micardis® and provides additional benefits against vascular and renal damage caused by diabetes and cardiovascular disease.[6-8]

Previously reported syntheses of telmisartan, including the commercial process, invariably rely on the sequential formation of the two benzimidazole moieties through cyclization of appropriately substituted aniline precursors. The high temperatures and extreme pH conditions required by this strategy result in lower yields and significant byproduct formation.

The original synthesis of telmisartan was developed by Ries et al. in 1993[10] (Scheme 1), beginning with the stepwise construction of the central benzimidazole ring from 4-amino-3-methylbenzoic acid methyl ester (2). Saponification of the resulting substituted benzimidazole 4 was followed by condensation with N-methyl-1,2-phenylenediamine (5) using polyphosphoric acid at elevated temperature (150° C.) to afford the functionalized dibenzimidazole 6. Alkylation of the latter with 4'-(bromomethyl)-2-biphenylcarboxylic acid tert-butyl ester (7) followed by hydrolysis of the resulting ester provided telmisartan in 21% overall yield over 8 linear steps.

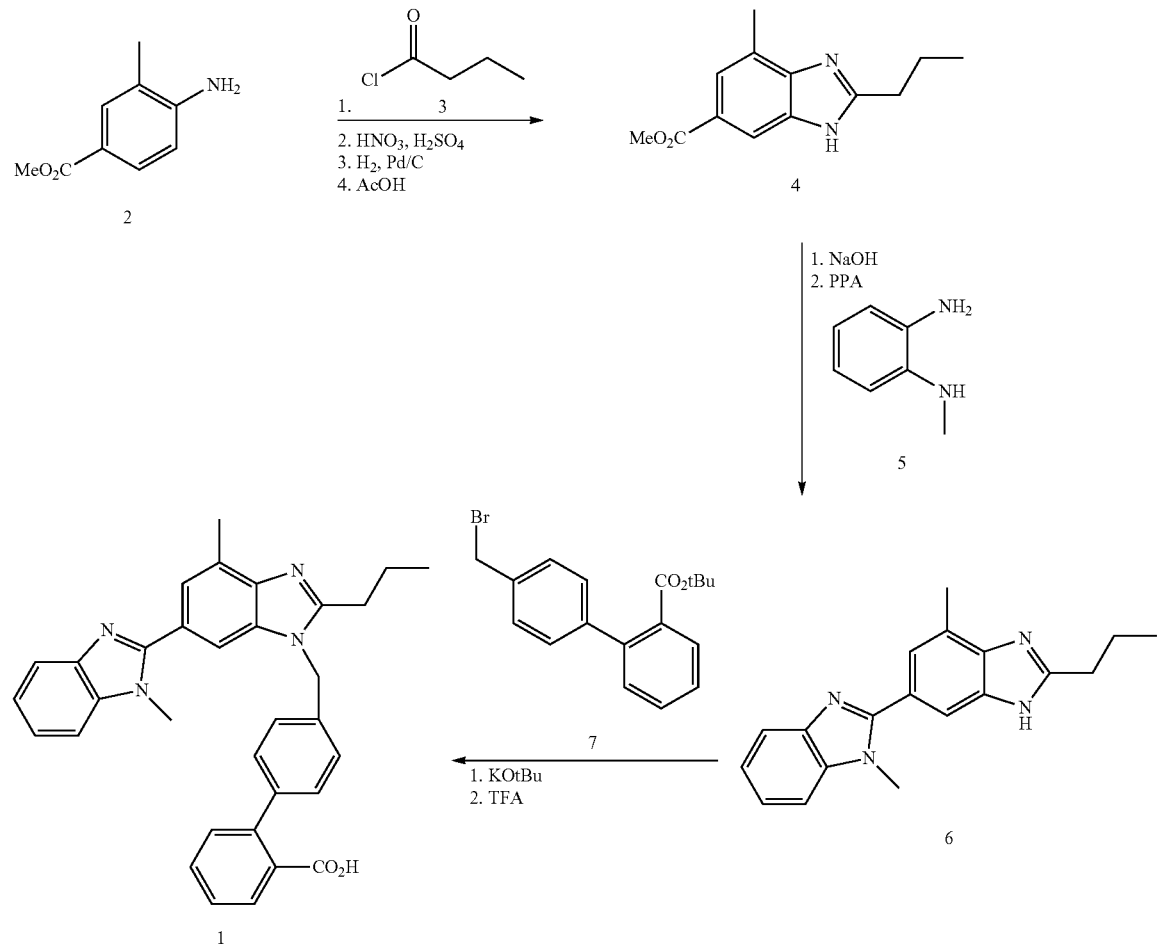

Scheme 1. Original Synthesis of Telmisartan

The elevated temperature and acidic conditions required during the second cyclization step adversely impact both product yield and purity—a major drawback of this original route that has not been addressed in subsequent process improvements to this basic method.[9,11-13] In a recent report, the cyclocondensation of an aromatic aldehyde with o-phenylenediamine was explored as an alternative path to the dibenzimidazole moiety, however this process still suffers from a rather low overall yield.[14] Other groups have taken advantage of cross-coupling reactions to build a formylated biphenyl fragment, avoiding the intricate and low-yielding preparation of 7 used in the original synthesis by substituting a reductive amination approach for the alkylation step.[15-17] Bypassing this alkylation reaction is no longer necessary because affordable analogs of bromide 7 are now commercially available. However, none of these modifications represent a significant departure from the original synthetic strategy nor have they remedied the major shortcomings associated with the formation of the dibenzimidazole component of the molecule.

There is a need in the art to provide a straightforward synthetic pathway for producing telmisartan of high purity in high yields.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The invention provides a fundamentally different approach to the synthesis of high-purity telmisartan in high yields. The synthesis is based on a novel Pd-catalyzed coupling of two structurally distinct benzimidazole units. This synthetic scheme is more convergent and higher yielding than recently reported efforts, reaching telmisartan in an overall yield of greater than 74%, in comparison to the previously reported highest yield of 50%.[9]

It is an object of this invention to provide a method of synthesizing telmisartan. The method comprises the step of coupling i) potassium(1-(2'-carboxy-[1,1'-biphenyl]-4-yl)-4-methyl-2-propyl-benzimidazole-6-yl) trifluoroborate and ii) 2-bromo-1-methylbenzimidazole, wherein the step of coupling is carried out under Suzuki cross-coupling reaction conditions, to form the telmisartan. In some aspects, the step of coupling is carried out using microwave assisted heating. In other aspects, the method further comprises the step of forming the potassium(1-(2'-carboxy-[1,1'-biphenyl]-4-yl)-4-methyl-2-propyl-benzimidazole-6-yl) trifluoroborate by i) pre-treating potassium(4-methyl-2-propyl-benzimidazole-6-yl) trifluoroborate with potassium tert-butoxide; and ii) alkylating pretreated potassium(4-methyl-2-propyl-benzimidazole-6-yl) trifluoroborate with methyl 4'-bromomethyl-biphenyl-2-carboxylate, to form the potassium(1-(2'-carboxy-[1,1'-biphenyl]-4-yl)-4-methyl-2-propyl-benzimidazole-6-yl) trifluoroborate. In yet other aspects, the method further comprises a step of forming the 2-bromo-1-methylbenzimidazole by regioselectively brominating a 2-position of 1-methylbenzimidazole to form 2-bromo-1-methylbenzimidazole. In additional aspects, the method further comprises the step of forming the potassium(4-methyl-2-propyl-benzimidazole-6-yl) trifluoroborate by i) performing reductive cyclization of 4-bromo-2-methyl-6-nitroaniline in the presence of n-butyraldehyde and sodium dithionite to form 6-bromo-4-methyl-2-propylbenzimidazole; and ii) converting the 6-bromo-4-methyl-2-propylbenzimidazole to a trifluoroborate salt, to form the potassium (4-methyl-2-propyl-benzimidazole-6-yl) trifluoroborate. In yet other aspects, the step of converting is performed by reacting the 6-bromo-4-methyl-2-propylbenzimidazole with diboron ester in the presence of a Pd catalyst to form a boronic acid pinacol ester; and converting the boronic acid pinacol ester to the potassium(4-methyl-2-propyl-benzimidazole-6-yl) trifluoroborate. In some aspects, the Pd catalyst is $PdCl_2dppf$. In some aspects, the step of converting is performed by reacting the 6-bromo-4-methyl-2-propylbenzimidazole with diboronic acid in the presence of a Pd catalyst to form 6-boronic acid-4-methyl-2-propylbenzimidazole; and contacting the 6-boronic acid-4-methyl-2-propylbenzimidazole with $KHF_2$ to form the potassium(4-methyl-2-propyl-benzimidazole-6-yl) trifluoroborate. In some aspects, the step of reacting is performed in the presence of a Pd catalyst; in further aspects, the Pd catalyst is $PdCl_2(PPh_3)_2$.

In some aspects of the invention, the step of coupling is catalyzed by a Pd catalyst. In further aspects, the Pd catalyst is a homogenous Pd catalyst; in some aspects, the homogenous Pd catalyst is $PdCl_2dppf$. In further aspects, the Pd catalyst is a heterogenous Pd catalyst; in some aspects, the heterogenous Pd catalyst is graphene supported Pd nanoparticles. In yet additional aspects, the step of regioselectively brominating is performed by brominating a 2-position of 1-methylbenzimidazole by, in a solution with tetrahydrofuran (THF) as solvent, contacting an imidazole ring of the 1-methylbenzimidazole with a brominating agent, to form the 2-bromo-1-methylbenzimidazole. In some aspects, the brominating agent is N-bromosuccinimide.

The invention also provides a method of regioselectively brominating a 2-position of an imidazole. The method comprises: in a solution with tetrahydrofuran (THF) as solvent, contacting the imidazole with a brominating agent to form an imidazole that is brominated at the 2-position. In some aspects, the imidazole is 1-methylbenzimidazole. In further aspects, the brominating agent is N-bromosuccinimide. In additional aspects, the step of contacting is carried out using microwave assisted heating.

DETAILED DESCRIPTION

The convergent synthesis of telmisartan provided herein entails the assembly of three major subunits: two differentially substituted benzimidazole derivatives and a biphenyl-2-carboxylic acid synthon (Scheme 2). This strategy provides for the use of a Suzuki cross-coupling reaction to form a new carbon-carbon bond between advanced isolated intermediates 2-bromo-1-methylbenzimidazole (8) and potassium (1-(2'-carboxy-[1,1'-biphenyl]-4-yl)-4-methyl-2-propyl-benzimidazole-6-yl) trifluoroborate (16), the latter of which is formed from the reaction of potassium (4-methyl-2-propyl-benzimidazol-6-yl) trifluoroborate (9) and methyl 4'-bromomethyl-biphenyl-2-carboxylate (10), followed by hydrolysis. The previous lack of a convenient and economical preparation protocol of one of the intermediates, 2-bromo-1-methylbenzimidazole 8, precluded development of such coupling strategies. However, as described herein, the present invention provides a novel, high yield synthetic method for preparing this intermediate, permitting its use in the present methods for synthesizing telmisartan.

Scheme 2. Retrosynthetic Analysis of Telmisartan

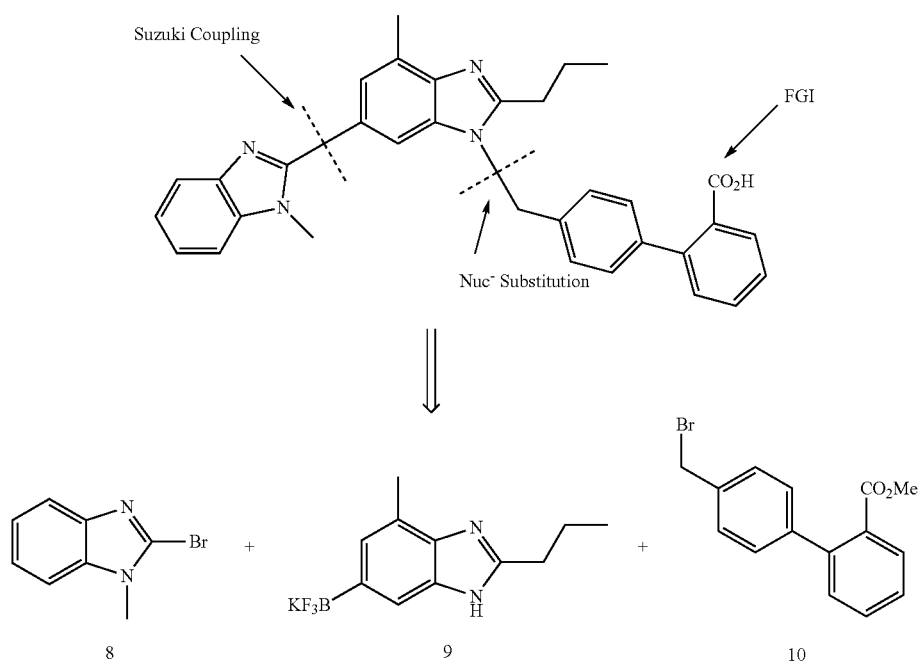

According to the synthetic method, which is described in detail in the Examples below, three major subunits including two differentially substituted benzimidazole derivatives [2-bromo-1-methylbenzimidazole (8) and potassium (4-methyl-2-propyl-benzimidazol-6-yl) trifluoroborate (9)] and a biphenyl-2-carboxylic acid synthon [methyl 4'-bromomethyl-biphenyl-2-carboxylate (10)] are assembled. Briefly, the biphenyl moiety is introduced via direct N-alkylation with commercially available methyl 4'-bromomethyl-biphenyl-2-carboxylate (10), followed by a saponification to the desired carboxylic acid. A Suzuki cross-coupling reaction is then used to form a new carbon-carbon bond between the two differentially substituted benzimidazole derivatives. This approach provides efficient assembly of the target molecule, while avoiding the harsh reaction conditions associated with the previous synthetic methods.

An advantage of this synthetic route to telmisartan is the use of regioselectively produced 2-bromo-1-methylbenzimidazole (8). Benzimidazoles are susceptible to reactions such as bromination at multiple sites. Thus, generally a mixture of mono, di- and tri-brominated by-products are formed and the particular reaction product that is wanted must be laboriously separated from the mixture. Further, the yields of such mixed reactions are generally unacceptably low. An aspect of the invention solves this problem by providing methods of synthesizing regio-selective benzimidazole adducts.

Accordingly, the inventors surprisingly discovered that regioselective bromination at a 2-position of an imidazole can be achieved by reacting the imidazole with a brominating agent in the solvent tetrahydrofuran (THF), which eliminates the formation of di- and tribromated products and other brominated products such as compound 8b below.

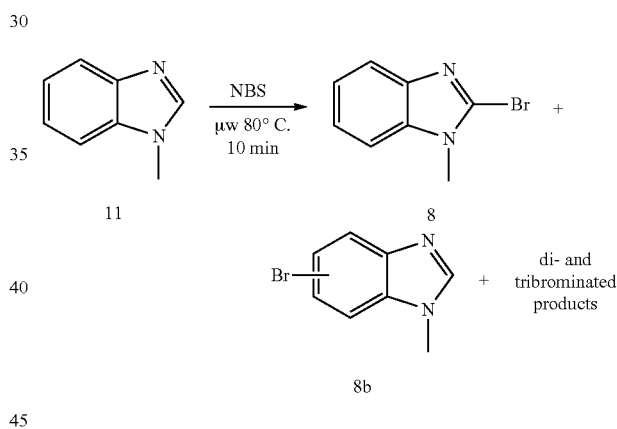

In some aspects, the imidazole is 1-methylbenzimidazole and the product is the desired reactant 2-bromo-1-methylbenzimidazole (8).

For this particular exemplary synthesis, commercially available 1-methylbenzimidazole (11) was reacted with the bromine source N-bromosuccinimide (NBS) in the solvent tetrahydrofuran (THF), and the reaction was carried out using microwave-assistance, as described in detail in the Examples section. However, other imidazoles may also be used as the starting material for the formation of regioselectively halogenated adducts as described herein, including but not limited to other N-alkylated benzimidazoles (in which the alkyl chain or may not have additional substituents), N-alkylated benzimidazoles (including 1-methyl) that have substituents on C4, C5, C6, or C7 of the benzene ring (e.g. substituents such as alkyl, aryl, various electron-withdrawing or electron-donating groups, etc.), and N-alkylated imidazoles with or without substitution at the 4 and 5 position. In addition, other bromine sources may be employed, including but not limited to molecular bromine, 1,3-dibromo-5,5-dimethylhydantoin (dibromantin), N-bromoacetamide, and N-bromosuccimide adducts (such as NBS-dimethyl formamide, NBS-dimethyl sulfide, NBS-hydrogen fluoride, NBS-sodium azide, and NBS-triphenylphospine). Further, halogens other than Br may be used to form halogenated imidazole adducts described herein, including but not limited to e.g. Cl, I, etc.

Other solvents may also be employed in the halogen adduct formation reaction, including but not limited to acetonitrile (ACN), diglyme, N-methylpyrrolidone (NMP), dimethyl sulfoxide (DMSO), dioxane, and water. In some aspects, the solvent that is used is not dimethylformamide (DMF), methanol (MeOH) or diethyl ether ($Et_2O$).

In addition, the reaction is not necessarily a "microwave-assisted" reaction, but instead may be carried out by more conventional heating e.g. by reflux.

The 2-bromo-1-methylbenzimidazole (8) that is formed as described above is one of two differentially substituted benzimidazole derivatives that are employed to carry out the novel convergent synthesis of telmisartan, the other being potassium(1-(2'-carboxy-[1,1'-biphenyl]-4-yl)-4-methyl-2-propyl-benzimidazole-6-yl) trifluoroborate (16).

The latter reactant (16) is formed by i) pre-treating potassium (4-methyl-2-propyl-benzimidazole-6-yl) trifluoroborate (9) with potassium tert-butoxide; and then ii) alkylating the pretreated potassium(4-methyl-2-propyl-benzimidazole-6-yl) trifluoroborate with methyl 4'-bromomethyl-biphenyl-2-carboxylate (10), as shown below.

Step i) of this reaction is generally carried out at room temperature with e.g. a 2-5 fold molar excess of potassium tert-butoxide in a solvent (such as DMSO, ACN, or NMP) with stirring for e.g. at least about 30 min. Step ii) is then performed by adding an equimolar (compared to compound (9)) amount of compound 10 to the reaction mixture with additional stirring at room temperature e.g. for at least about 1, and typically at least about 2 hours. A solution of e.g. about 5-fold molar excess (compared to compound (9)) of a suitable base (such as KOH, NaOH, LiOH, etc. dissolved in an aqueous solvent such as $H_2O$) is then added to the reaction mixture, which is then stirred for several more hours (e.g. about 3-8) hours at room temperature. The solution is then made acidic, e.g. by adjusting the pH to at least about pH 4 with a suitable acid source, and a white precipitate is produced which is filtered and rinsed with a suitable solvent (e.g. THF) and dried. The product is potassium(1-(2'-carboxy-[1,1'-biphenyl]-4-yl)-4-methyl-2-propyl-benzimidazole-6-yl) trifluoroborate (16).

In some aspects, reactant (9), potassium (4-methyl-2-propyl-benzimidazole-6-yl) trifluoroborate is formed by i) performing reductive cyclization of 4-bromo-2-methyl-6-nitroaniline in the presence of n-butyraldehyde and sodium dithionite to form 6-bromo-4-methyl-2-propylbenzimidazole; and ii) converting the 6-bromo-4-methyl-2-propylbenzimidazole to a trifluoroborate salt to form reactant (9). In some aspects, the step ii) is performed by: mixing, in a suitable solvent (such as DMSO, dioxane, THF, ACN, or toluene) about a 2-fold molar excess of bis(pinacolato)diboron (15) with 6-bromo-4-methyl-2-propylbenzimidazole (14) and excess KOAc in the presence of a catalyst, such as a Pd catalyst; heating (e.g. to at least about 100° C., using any suitable heating method) under nitrogen for e.g. about 3-7 hours; cooling and extracting (e.g. with EtOAc) and then concentrating the organic phase; dissolving the residue in a suitable solvent (e.g. THF) and reacting the same with potassium bifluoride ($KHF_2$) at room temperature for e.g. about 3-7 h. Removal of the solvent, precipitation and rinsing yields (9).

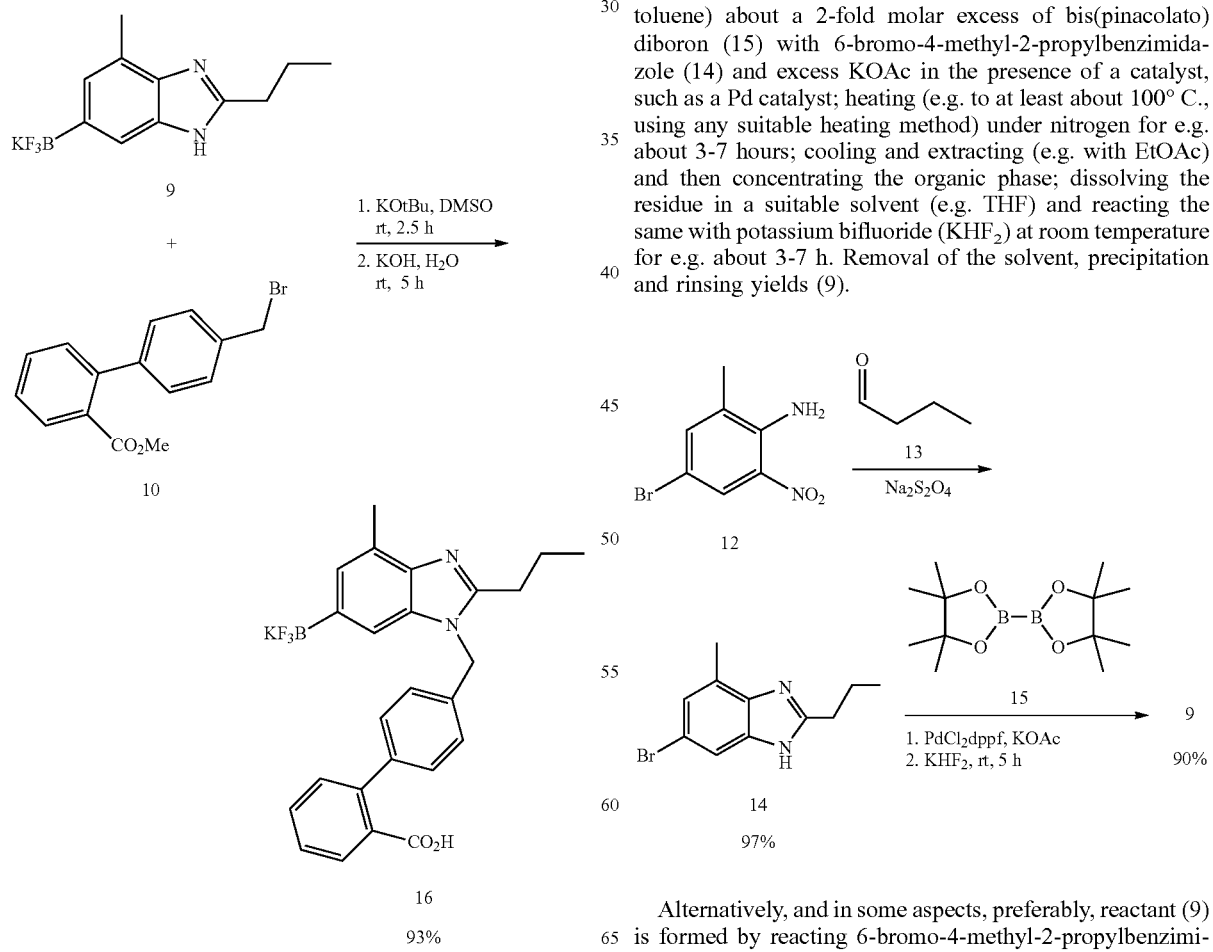

Alternatively, and in some aspects, preferably, reactant (9) is formed by reacting 6-bromo-4-methyl-2-propylbenzimidazole with diboronic acid in the presence of a Pd catalyst, and is then treated with $KHF_2$ to form (9).

To form the final product, telmisartan (1), compound (16) is reacted with 2-bromo-1-methylbenzimidazole (8).

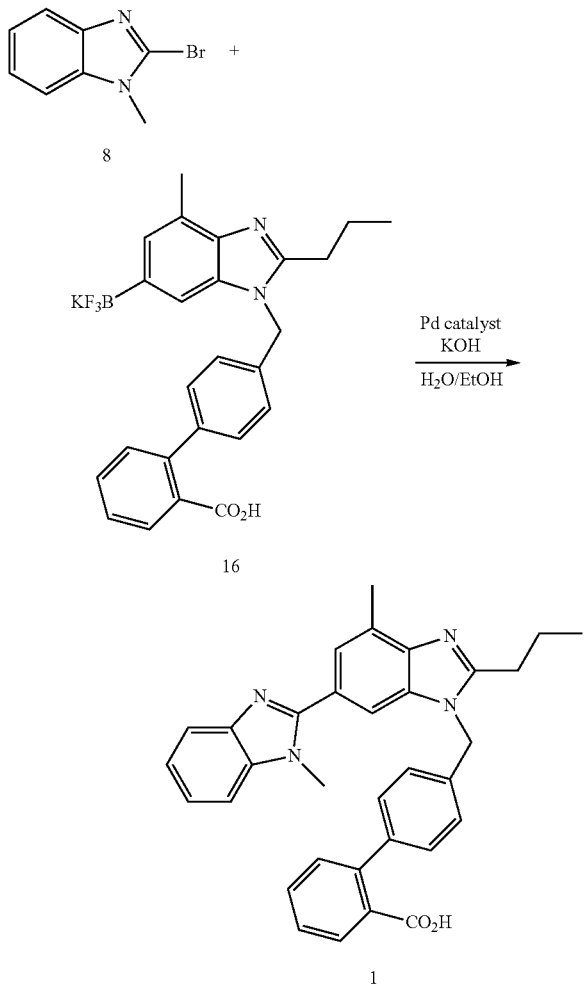

In some aspects, compound (8) is made using the novel regio-selective bromination reaction described above. However, the use of other sources of (8), e.g. commercial sources, and/or 8 produced by different reactions, is not excluded. Due to the availability of the starting material 8 in high yield and purity as described herein, and the ready synthesis of starting material 16, the final reaction step is a Suzuki cross-coupling reaction. Briefly, equimolar amounts of compounds 8 and 16 and a 2-fold molar excess of base are combined in aqueous ethanol, e.g. a 1:1 mixture of $H_2O$ and EtOH, in the presence of a catalyst such as a Pd catalyst. The solution is heated with stirring e.g. to greater than about 100° C. for at least 30 minutes or longer, e.g. for about 1-2 hours. Any suitable heating method may be used. However, in some aspects, the reaction is carried out rapidly by heating to 150° C. using microwave irradiation, for example, for from about 15 to about 45 minutes, e.g. for about 30 minutes. The solution is then filtered, brought to a desired volume with a suitable solvent (e.g. $H_2O$) and the pH was adjusted to acidity, e.g. to at least about 5 or lower, using a suitable acid. The resulting precipitate is filtered and dried, yielding telmisartan.

In some aspects, one or more of the reactions described herein is catalyzed using a Pd catalyst. Exemplary Pd catalysts that may be used include but are not limited to: various homogeneous palladium catalysts such as $PdCl_2(PPh_3)_2$, $PdCl_2dppf$, $Pd(PPh_3)_4$, and others (e.g. see issued U.S. Pat. Nos. 8,889,857 and 8,981,086), etc.; or homogeneous palladium catalysts formed in situ from precatalysts such as but not limited to $Pd(OAc)_2$ or $Pd_2(dba)_3$ and an exogenous ligand source such as but not limited to trialkylphosphines such as triphenylphosphine or tri-tert-butylphosphine, dialkylbiarylphosphines such as 2-(dicyclohexylphosphino)biphenyl or SPhos, N-heterocyclic carbene (NHC) ligands such as those formed from 1,3-bis(2,6-diisopropylphenyl)imidazolium chloride, diimines, BINAP-based ligands, bidentate phosphino ligands, etc, and others (e.g. see, for example, informational brochures located at acros.com/myBrochure/Catalysts, Maluenda et al. *Molecules* 2015, 20, 7528-7557 and Hanhan, *Appl. Organometail Chem.* 2008, 22, 270-275); or heterogeneous Pd catalysts such as solid-supported catalysts, including graphene-supported Pd nanoparticles, Pd nanoparticles on single- or multi-walled carbon nanotubes, Pd on other solid supports such as silica-based matrices, or Pd that exists that exists in trace levels in earth abundant metals such as iron, e.g. $FeCl_3$, (for example, see Handa et al., *Science*, 2015, 349, 1087-1091). In preferred embodiments, the Pd catalyst is graphene-supported Pd nanoparticles. In other preferred embodiments, the Pd catalyst is $PdCl_2dppf$.

In other aspects, one or more of the reactions described herein is catalyzed using a Ni catalyst. Exemplary Ni catalysts that may be used include but are not limited to: bis(triphenylphosphine)nickel(II)chloride; bis(triphenylphosphine)nickel(II)bromide; [1,3-Bis(diphenylphosphino)propane]nickel(II)chloride; $NiX_2$, where X=Cl, Br, I, etc., with an exogenous ligand source such as but not limited to triphenylphosphine, tricyclohexylphosphine, dppf, BINAP, and other ligands (e.g. see Tasker et al. *Nature*, 2014, 509, 299-309; Ge et al., *Angew. Chem. Int. Ed. Eng.* 2012, 51, 12837-12841; and informational brochures located at acros.com/myBrochure/Catalysts), (dppf)Ni(cinnamyl)Cl; (NHC)Ni(Cp)X, where X=Cl, Br, etc.; (NHC)Ni(0), (NHC)nN(II); as well as Ni catalysts disclosed in US patent applications 20100184977; 2012006544; 20140134101; 20140336429; and 20150166556 and in issued U.S. Pat. Nos. 8,822,368, 8,956,428 and 9,051,524.

Several of the reactions described herein require or are preferably performed with heating. Any suitable method of heating may be used, e.g. conventional waterbaths, heating plates, incubators, etc. However, frequently, the reaction time may be shortened and yield may be increased by the use of microwave-assisted heating. In this case, temperatures of at least 100° C. or greater (e.g. 110, 120, 130, 140, or 150° C.) are readily achieved. The reactions described herein may be conducted using any of these heating methods to achieve the requisite temperatures, and/or may even be carried out at other temperatures than those listed herein, by adjusting the reaction time accordingly.

Provided herein are methods comprising chemical reactions that are used to make telmisartan, as well as telmisartan that is produced using the methods. In addition, drug formulations of telmisartan that is so-produced are encompassed. The formulations are generally prepared either as liquids (e.g. aqueous or oil-based suspensions or solutions) or as solid forms such as tablets, pills, powders and the like, in combination with a physiologically acceptable carrier. Solid forms suitable for solution in, or suspension in, liquids prior to administration may also be prepared. The telmisartan may be mixed with excipients which are pharmaceutically acceptable e.g. pharmaceutically acceptable salts. The composition of the present invention may contain any such additional ingredients so as to provide the composition in a form suitable for administration. The final amount of telmisartan in the formulations may vary. However, in general, the amount in the formulations will be from about 1-99%. Still other suitable formulations for use in the present invention can be found, for example in Remington's Pharmaceutical Sciences, Philadelphia, Pa., 19th ed. (1995).

EXAMPLES

Example 1. A Convergent Approach to the Total Synthesis of Telmisartan Via a Suzuki Cross-Coupling Reaction Between Two Functionalized Benzimidazoles A direct and efficient total synthesis has been developed for telmisartan, a widely prescribed treatment for hypertension. This approach brings together two functionalized benzimidazoles using a high-yielding Suzuki reaction that can be catalyzed by either a homogeneous palladium source or graphene-supported palladium nanoparticles. The ability to perform the cross-coupling reaction was facilitated by the regio-controlled preparation of the 2-bromo-1-methylbenzimidazole precursor. This convergent approach provides telmisartan in an overall yield of 72% while circumventing many issues associated with previously reported processes.

As stated in the Detailed Description, the convergent synthesis of telmisartan entails the assembly of three major subunits: two differentially substituted benzimidazole derivatives and a biphenyl-2-carboxylic acid synthon (Scheme 2). In general, a Suzuki cross-coupling reaction is used to form a new carbon-carbon bond between two differentially substituted benzimidazole derivatives, and the biphenyl moiety is introduced via direct N-alkylation with commercially available methyl 4'-bromomethyl-biphenyl-2-carboxylate (10), followed by a saponification to the desired carboxylic acid. This approach provides efficient assembly of the target molecule, while avoiding the harsh reaction conditions associated with the previous synthetic methods.

Initial efforts focused on preparation of 8, a strategic element in the Suzuki coupling reaction. Starting with commercially available 1-methylbenzimidazole (11), we were able to identify reaction conditions to selectively brominate the imidazole ring with N-bromosuccinimide (NBS). While benzimidazoles can be susceptible to bromination at multiple sites[18] resulting in the formation of a mixture of mono-, di- and tri-brominated by-products, our major challenge was to identify conditions by which bromination could be achieved exclusively at the 2-position in high yield. A solvent screen of microwave-assisted reactions revealed that dichloromethane (DCM), methanol, dimethylformamide (DMF), and diethyl ether yield mainly undesired mixtures of byproducts (Table 1, entries 1-4), but tetrahydrofuran (THF) affords essentially complete conversion to the desired product (entry 5). Similar selectivity trends were observed during solvent screening under conventional reaction conditions (not shown), and we were able to achieve an isolated yield of 93% with the THF under reflux conditions. To our knowledge, this is the first example of a selective and scalable bromination of 1-methylbenzimidazole at the 2-position and was an essential element of our convergent strategy. This procedure should find utility in the preparation of other benzimidazole adducts.

TABLE 1

Bromination of 1-Methylbenzimidazole[a]

| entry | solvent | 8[b] | 8b[b] | di- and tri-bromination[b] |
|---|---|---|---|---|
| 1 | DCM | 0 | 0 | 100 |
| 2 | DMF | 0 | 8 | 92 |
| 3 | MeOH | 0 | 12 | 88 |
| 4 | Et$_2$O | 0 | 27 | 73 |
| 5 | THF | 100 | 0 | 0 |
| 6[c] | THF | 93[d] | 0 | 0 |

[a]11 (0.76 mmol), NBS (2.3 mmol), 4 mL solvent.
[b]% Conversions determined by GC-MS.
[c]Reaction ran under reflux for 1 h.
[d]Isolated yield.

In order to establish the necessary precursors for a Suzuki-based approach to the dibenzimidazole core of telmisartan, we elected to prepare the trifluoroborate salt 9 starting from commercially available 4-bromo-2-methyl-6-nitroaniline (12). Compound 12 could be easily converted to benzimidazole 14 in a single step. This reductive cyclization, provoked by introducing n-butyraldehyde (13) in the presence of sodium dithionite,[14] produced 14 in 97% isolated yield (Scheme 3). This approach represents a significant improvement over the originally reported method: benzimidazole formation can be completed in a single step, compared to the problematic three-step sequence (amidation, reduction and cyclization) of Ries et al.[10] Moreover, sodium dithionite provides an effective and inexpensive alternative to the palladium catalyst typically used for reduction of the nitro group. Avoiding palladium in this case is particularly beneficial as the aryl bromide is susceptible to dehalogenation under Pd-catalyzed hydrogenation conditions.[19]

Scheme 3. Synthesis of Compound 9.

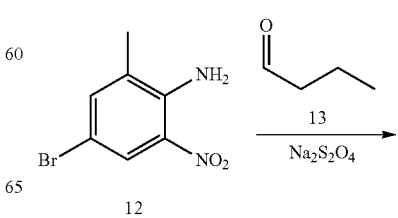

-continued

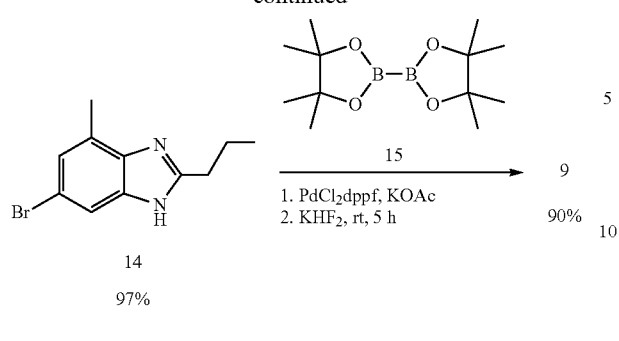

14
97%

Benzimidazole 14 was then converted to the trifluoroborate salt 9 in two steps with no isolated intermediate. We originally chose to introduce the boron species as the pinacol ester.[20] The reaction of 6-bromo-4-methyl-2-propylbenzimidazole (14) and diboron 15 (2 equiv.) at 100° C. for 5 hours in the presence of PdCl$_2$dppf (5 mol %) led to the formation of the desired boronic acid pinacol ester. We converted this pinacol boronate directly to the corresponding trifluoroborate salt,[21] as trifluoroborates tend to be significantly more reactive toward Suzuki cross-coupling reactions.[22-24] The yield from this two-step process is 90% from benzimidazole 14. Isolation of trifluoroborate 9 is straightforward, as it can be precipitated out of the reaction mixture in pure form.

Most of the previous telmisartan syntheses employed a common strategy in which the dibenzimidazole moiety was prepared first, followed by the installation of the biphenyl group. However, we chose to alkylate benzimidazole 9 prior to the Suzuki reaction in order to avoid an observed side reaction between 8 and 9.[25] The N-alkylation of 9 with bromide 10 was carried out in DMSO under basic reaction conditions (Scheme 4). Notably, we found it necessary to pre-treat 9 with potassium tert-butoxide to avoid the formation of unwanted Williamson ether byproducts. Furthermore, we developed reaction conditions to telescope saponification of the methyl ester with the alkylation step, achieving a 93% yield of 16 over these two chemical steps.

Scheme 4. One-pot Synthesis of Compound 16

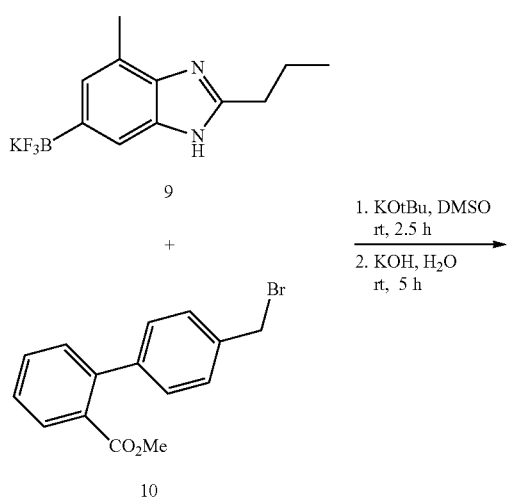

-continued

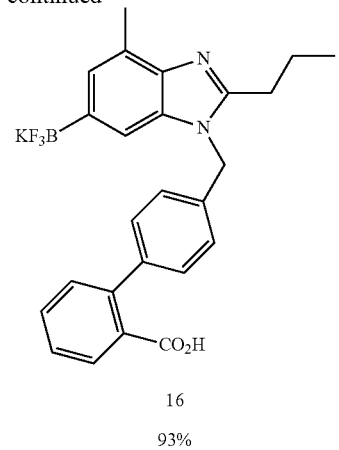

16
93%

The final coupling reaction of 16 with 8 was carried out under Suzuki cross-coupling reaction conditions[26,27] using PdCl$_2$dppf with KOH in a H$_2$O/EtOH solvent system. Under atmospheric reflux conditions, the reaction afforded telmisartan in a low to moderate yield (Table 2, entries 1 and 2). In order to achieve higher temperatures with this same solvent system, reactions were then run under elevated pressure using microwave heating. Using this strategy, reaction times were significantly reduced, and isolated yields showed some improvement. We then applied a factorial design of experiment approach in order to identify the set of reaction parameters that would maximize yield while minimizing catalyst loading (not shown). Optimized Suzuki reaction conditions (Table 2, entry 3) generated telmisartan in 89% isolated yield using only 2 mol % catalyst. We expect that similar results can be achieved under elevated pressures with conventional heating.

Pd nanoparticles supported on graphene (Pd/G)[28] demonstrate remarkable catalytic activity and recyclability in a wide range of Suzuki cross coupling reactions. Thus, we were interested in evaluating this catalyst system for the Suzuki cross coupling step of our telmisartan synthesis. Preliminary experiments using just 2 mol % of Pd/G under microwave irradiation conditions led to the formation of the desired product with 76% isolated yield (Table 2, entry 4). Furthermore, the catalyst was recycled for two further reactions under the same conditions without appreciable reduction in isolated yield. This catalyst system can also be employed in both batch and continuous processes for the assembly of telmisartan.

TABLE 2

Suzuki Cross-coupling to form Telmisartan$^a$

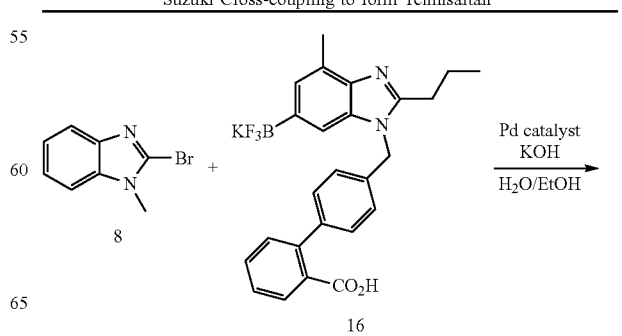

TABLE 2-continued

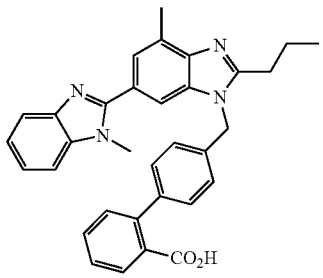

1

| entry | catalyst | conditions | 1[b] |
|---|---|---|---|
| 1 | PdCl$_2$dppf (2 mol %) | reflux, 15 h | 36 |
| 2 | PdCl$_2$dppf (10 mol %) | reflux, 15 h | 55 |
| 3[c] | PdCl$_2$dppf (2 mol %) | µw 150° C., 30 min | 89 |
| 4[c,d] | Pd/G (2 mol %) | µw 150° C., 20 min | 76 |

[a]8 (0.19 mmol), KOH (0.57 mmol), 4 mL H$_2$O/EtOH (1:1 mixture).
[b]Isolated yield.
[c]Reactions were carried out under microwave irradiation at 150° C., generating a pressure of 18 atm inside the microwave tube.
[d]Pd/G catalyst was recycled an additional 2 times affording 68 and 62% isolated yields, respectively.

In summary, a concise and convergent synthesis of the anti-hypertensive drug telmisartan has been achieved. With an overall yield of 72%, our strategy represents a significant improvement over the highest yield reported previously[9] (50%). Our approach features an efficient Pd-catalyzed Suzuki reaction between two intact benzimidazole moieties as the final reaction step, enabled by the development of a regioselective bromination of 1-methylbenzimidazole. In addition, the harsh reaction conditions that have plagued the commercial route have been avoided. Our synthetic route also illustrates the potential of graphene-supported Pd nanoparticles (Pd/G) as an alternative catalytic source for cross-coupling reactions. Finally, our strategy has a very efficient endgame, as each step to assemble telmisartan from the key synthons is high-yielding (83% over the final 3 steps, from trifluoroborate 9). From a broader perspective, dibenzimidazoles represent an important class of pharmacophores, and this report describes a selective and straightforward method for the preparation of these privileged structures.

Experimental Section

2-Bromo-1-methylbenzimidazole (8)

1-methylbenzimidazole (11) (5.0 g, 37.8 mmol) and N-bromosuccinimide (20.2 g, 113.5 mmol) in 200 mL of THF was heated under reflux for 1 h. The solvent was removed in rotary evaporator and the residue was recrystallized from EtOAc yielding 8 (7.4 g, 93%) as a white solid. $^1$H NMR (DMSO-d$_6$) δ 7.77 (d, 1H), 7.65 (d, 1H), 7.39 (m, 2H), 3.86 (s, 3H); $^{13}$C NMR (DMSO-d$_6$) δ 138.2, 135.4, 131.5, 124.8, 124.7, 117.0, 112.3, 33.0; HRMS (ESI-QTOF): m/z Calcd for C$_8$H$_7$N$_2$Br+H$^+$: 210.9871, found: 210.9911.

6-Bromo-4-methyl-2-propylbenzimidazole (14)

n-Butyraldehyde (13) (3.1 mL, 34.6 mmol) was added to a 250 mL flask containing 4-bromo-2-methyl-6-nitroaniline (12) (4.0 g, 17.3 mmol) and sodium dithionite (18.1 g, 103.9 mmol) in 80 mL of 50% MeOH in H$_2$O. The reaction was stirred at reflux for 5 h. The methanol was removed via rotary evaporator. To the remaining aqueous solution, an additional 40 mL of water was added and the mixture was extracted using EtOAc (3×80 mL). The organic layer was dried using magnesium sulfate. After filtration, the organic layer was removed via rotary evaporator and the resulting solid was dried in the oven producing 13 as a white solid (4.3 g, 97%). $^1$H NMR (DMSO-d$_6$) δ 7.47 (s, 1H), 7.08 (s, 1H), 2.77 (t, 2H), 2.47 (s, 3H), 1.79 (m, 2H), 0.95 (t, 3H); $^{13}$C NMR (DMSO-d$_6$) δ 155.7, 124.0, 113.1, 30.5, 20.9, 16.4, 13.6; HRMS (ESI-QTOF): m/z Calcd for C$_{11}$H$_{13}$N$_2$Br+H$^+$: 253.0340, found: 253.0446.

Potassium (4-methyl-2-propyl-benzimidazol-6-yl) trifluoroborate (9)

6-Bromo-4-methyl-2-propylbenzimidazole (14) (2.0 g, 7.9 mmol) and bis(pinacolato) diboron (15) (4.0 g, 15.8 mmol) were added to a flask along with KOAc (2.3 g, 23.7 mmol) and PdCl$_2$dppf (289 mg, 0.4 mmol). DMSO (20 mL) was added, the flask was evacuated and placed under nitrogen. The solution was heated at 100° C. for 5 h. The reaction mixture was cooled followed by the addition of 80 mL H$_2$O and extracted with EtOAc (3×100 mL). The organic layer was combined and concentrated by rotary evaporation. The resulting residue was then taken up in THF (32 mL) and combined with a solution of potassium bifluoride (3.1 g, 39.5 mmol) in H$_2$O (8 mL). The combined solution was stirred at room temperature for 5 h. Upon removal of the THF, the precipitate was filtered and rinsed using EtOAc, yielding 9 as a white solid (2.0 g, 90%). $^1$H NMR (DMSO-d$_6$) δ 7.36 (s, 1H), 7.25 (s, 1H), 3.01 (t, 2H), 2.48 (s, 3H), 1.85 (m, 2H), 0.94 (t, 3H); $^{13}$C NMR (DMSO-d$_6$) δ 152.5, 130.7, 129.3, 121.4, 113.0, 28.5, 21.0, 17.1, 14.0; HRMS (ESI-QTOF): m/z Calcd for C$_{11}$H$_{13}$N$_2$BF$_3$K+H$^+$: 281.0839, found: 281.0901.

Potassium(1-(2'-carboxy-[1,1'-biphenyl]-4-yl)-4-methyl-2-propyl-benzimidazole-6-yl) trifluoroborate (16)

Compound 9 (2.0 g, 7.1 mmol) was added to a solution of KOtBu (2.4 g, 21 mmol) in DMSO (20 mL) and stirred for 30 min at room temperature. Compound 10 (2.2 g, 7.1 mmol) was then added to the reaction mixture and stirred for 2 h at room temperature. A solution of 2 g KOH (35 mmol) in H$_2$O (80 mL) was then added to the reaction mixture and stirred for an additional 5 h at room temperature. The solution was adjusted to pH 4 using AcOH, producing a white precipitate. The precipitated material was filtered, rinsed with THF and then dried, yielding a white solid (3.2 g, 93% yield). $^1$H NMR (DMSO-d$_6$) δ 7.22-7.72 (m, 10H), 5.80 (s, 2H), 3.19 (t, 2H), 2.54 (s, 3H), 1.76 (m, 2H), 0.96 (t, 3H); $^{13}$C NMR (DMSO-d$_6$) δ 170.2, 152.8, 141.2, 141.0, 134.8, 132.2, 131.6, 131.2, 129.8, 129.5, 129.4, 128.1, 126.9, 122.2, 112.1, 47.4, 27.3, 21.5, 17.1, 14.1; HRMS (ESI-QTOF): m/z Calcd for C$_{25}$H$_{23}$O$_2$N$_2$BF$_3$K+H$^+$: 491.1520, found: 491.1783.

Telmisartan (1)

2-bromo-1-methyl-benzimidazole 8 (40 mg, 0.19 mmol) and 16 (97.6 mg, 0.20 mmol) were combined with KOH (31.9 mg, 0.57 mmol) and 2 mol % PdCl$_2$dppf (2.8 mg, 0.004 mmol) in a 1:1 mixture of H$_2$O and EtOH (4 mL). The solution was heated using microwave irradiation, in a sealed tube, with stirring for 30 minutes at 150° C. The solution was filtered through Celite®. To the filtrate, 10 mL of H$_2$O was added and the pH was adjusted to 4 using AcOH. The resulting precipitate was filtered and dried in oven producing telmisartan (86.7 mg, 89% yield). $^1$H NMR (CDCl$_3$) δ 8.41 (d, 1H), 8.04 (d, 1H), 7.00-7.52 (m, 12H), 5.43 (s, 2H), 3.76 (s, 3H), 3.16 (t, 2H), 2.73 (s, 2H), 2.02 (m, 2H), 1.18 (t, 3H); $^{13}$C NMR (CDCl$_3$) δ 172.9, 158.2, 155.7, 145.2, 144.5, 143.3, 142.7, 137.2, 136.2, 135.6, 135.3, 132.1, 131.9, 131.0, 130.6, 130.4, 129.0, 128.8, 125.2, 124.9, 124.8, 123.5, 121.4, 113.0, 111.0, 50.5, 33.5, 31.7, 24.1, 18.6, 15.8; HRMS (ESI-QTOF): m/z Calcd for C$_{33}$H$_{30}$O$_2$N$_4$+H$^+$: 515.2447, found: 515.2468.

Procedure for Preparation of Pd Nanoparticles Supported on Graphene (Pd/G)

Pd nanoparticles supported on graphene (Pd/G) was prepared according to the procedure developed previously.[28] Graphite oxide (100 mg) and the palladium nitrate (194 μL of 10 wt. % in 10 wt. % HNO$_3$, 99.999%) were sonicated in deionized water until a yellow dispersion was obtained. The solution was placed inside a conventional microwave after adding 100 μl of the reducing agent hydrazine hydrate. The microwave oven (Emerson MW8119SB) was then operated at full power (1000 W), 2.45 GHz, in 30 s cycles (on for 10 s, off and stirring for 20 s) for a total irradiation time of 60 s. The yellow solution of Pd nitrate-graphite oxide changed to a black color indicating the completion of the chemical reduction to graphene. The Pd/G nanoparticles were separated by using an Eppendorf 5804 centrifuge operated at 5000 rpm for 15 min and dried overnight under vacuum.

Procedure for Suzuki Cross Coupling Reaction Using Pd/G and Recycling the Heterogeneous Catalyst 2-bromo-1-methyl-benzimidazole 8 (20 mg, 0.094 mmol) was dissolved in a mixture of 2 mL H$_2$O:EtOH (1:1) and placed in a 10 mL microwave tube. To this was added 16 (48.8 mg, 0.099 mmol), and potassium hydroxide (21.3 mg, 0.38 mmol). The palladium on graphene catalyst (Pd/G) (2.5 mg, 1.9 μmop was then added, and the tube was sealed and heated under microwave irradiation (250 W, 2.45 MHz) at 150° C. for 20 minutes. Upon the completion of the reaction period, the reaction mixture was diluted with 2 mL of 10 mg/mL KOH in EtOH and centrifuged to remove the solid catalyst. The EtOH/KOH washing were repeated twice to ensure the complete dissolution of the product from the surface of the catalyst. The solution was decanted and the solvent was partially concentrated in vacuo. After adjusting the pH of the remaining solution to 4 using AcOH, the precipitated telmisartan product was isolated by filtration and dried in the oven (76% isolated yield). In case of recycling the Pd/G nanoparticles, the solid catalyst was removed by centrifugation and added to the next reaction mixture using fresh reagents as indicated above. The reaction solution was heated in the microwave at 150° C. for 20 minutes and the same purification was applied, affording telmisartan with an isolated yield of 68 and 62% in the second and third reactions, respectively.

REFERENCES FOR EXAMPLE 1

(1) Wienen, W.; Hauel, N.; Van Meel, J. C. A.; Narr, B.; Ries, U.; Entzeroth, M. *Br. J. Pharmacol.* 1993, 110, 245-252.
(2) Battershill, A. J.; Scott, L. J. *Drugs* 2006, 66, 51-83.
(3) McClellan, K. J.; Markham, A. *Drugs* 1998, 56, 1039-1044.
(4) Cernes, R.; Mashavi, M.; Zimlichman, R. *Vasc. Health Risk Manag.* 2011, 7, 749-759.
(5) Burnier, M.; Brunner, H. R. *Lancet* 2000, 355, 637-645.
(6) Benson, S. C.; Pershadsingh, H. A.; Ho, C. I.; Chittiboyina, A.; Desai, P.; Pravenec, M.; Qi, N.; Wang, J.; Avery, M. A.; Kurtz, T. W. *Hypertension* 2004, 43, 993-1002.
(7) Benndorf, R. A.; Rudolph, T.; Appel, D.; Schwedhelm, E.; Maas, R.; Schulze, F.; Silberhorn, E.; Boger, R. H. *Metab. Clin. Exp.* 2006, 55, 1159-1164.
(8) Mann, J. F. E.; Schmieder, R. E.; McQueen, M.; Dyal, L.; Schumacher, H.; Pogue, J.; Wang, X.; Maggioni, A.; Budaj, A.; Chaithiraphan, S.; Dickstein, K.; Keltai, M.; Metasärinne, K.; Oto, A.; Parkhomenko, A.; Piegas, L. S.; Svendsen, T. L.; Teo, K. K.; Yusuf, S. *Lancet* 2008, 372, 547-553.
(9) Reddy, K. S.; Srinivasan, N.; Reddy, C. R.; Kolla, N.; Anjaneyulu, Y.; Venkatraman, S.; Bhattacharya, A.; Mathad, V. T. *Org. Proc. Res. Dev.* 2007, 11, 81-85.
(10) Ries, U. J.; Mihm, G.; Narr, B.; Hasselbach, K. M.; Wittneben, H.; Entzeroth, M.; Van Meel, J. C. A.; Wienen, W.; Hauel, N. H. *J. Med. Chem.* 1993, 36, 4040-4051.
(11) Hauel, N.; Dach, R.; Heitger, H.; Meyer, O. U.S. Patent 2004, 0236113A1.
(12) Kankan, R. N.; Rao, D. R.; Srinivas, P. L.; Ravikumar, P. U.K. Patent 2005, GB2414019A.
(13) Rao, C. H.; Naresh, T.; Satyanarayana, K.; Reddy, B. R.; Reddy, G. M. *Synth. Commun.* 2010, 40, 530-534.
(14) Wang, P.; Zheng, G.; Wang, Y.; Wang, X.; Wei, H.; Xiang, W. *Tetrahedron.* 2012, 68, 2509-2512.
(15) Goosen, L. J.; Knauben, T. *J. Org. Chem.* 2008, 73, 8631-8634.
(16) Kumar, A. S.; Ghosh, S.; Mehta, G. N.; Soundararajan, R.; Sarma, P. S. R.; Bhima, K. *Synth. Commun.* 2009, 39, 4149-4157.
(17) Kumar, A. S.; Ghosh, S.; Mehta, G. N. *Beilstein J. Org. Chem.* 2010, 6, No. 25.
(18) Mistry, A. G.; Smith, K. *Tetrahedron Lett.* 1986, 27, 1051-1054.
(19) Alonso, F.; Beletskaya, I. P.; Yus, M. *Chem. Rev.* 2002, 102, 4009-4091.
(20) Velaparthi, U.; Wittman, M.; Liu, P.; Carboni, J. M.; Lee, F. Y.; Attar, R.; Balimane, P.; Clarke, W.; Sinz, M. W.; Hurlburt, W.; Patel, K.; Discenza, L.; Kim, S.; Gottardis, M.; Greer, A.; Li, A.; Saulnier, M.; Yang, Z.; Zimmermann, K.; Trainor, G.; Vyas, D. *J. Med. Chem.* 2008, 51, 5897-5900.
(21) Murphy, J. M.; Tzschucke, C. C.; Hartwig, J. F. *Org Lett.* 2007, 9, 757-760.
(22) Molander, G. A.; Biolatto, B. *J. Org. Chem.* 2003. 68, 4302-4314.
(23) Darses, S.; Genet, J. P. *Eur. J Org. Chem.* 2003, 4313-4327.
(24) Molander, G. A.; Canturk, B.; Kennedy, L. E. *J. Org. Chem.* 2009, 74, 973-980.
(25) Displacement of the bromide on benzimidazole 8 by the nucleophilic nitrogen of 9 was observed to compete with the desired Suzuki coupling between 8 and 9.
(26) Miyaura, N.; Suzuki, A. *Chem. Rev.* 1995, 95, 2457-2483.
(27) Bellina, F.; Carpita, A.; Rossi, R. *Synthesis* 2004, 15, 2419-2440.

(28) Siamaki, A. R.; Khder, A. E. R. S.; Abdelsayed, V.; El-Shall, M. S.; Gupton, B. F. *J. Catal.* 2011, 279, 1-11.

Example 2. Synthesis of potassium (4-methyl-2-propyl-benzimidazole-6-yl) trifluoroborate (9) Using Diboronic Acid Reactant (9) may also be synthesized by reacting 6-bromo-4-methyl-2-propylbenzimidazole with diboronic acid in the presence of a Pd catalyst, followed by treatment with $KHF_2$, as follows: The reaction of 6-bromo-4-methyl-2-propylbenzimidazole (14) and diboronic acid (3 equiv.) at 75° C. for 10 hours in the presence of $PdCl_2PPh_3$ (3 mol %), triphenylphosphine (4 mol %) and potassium acetate (3 equiv.) led to the formation of the desired boronic acid. This intermediate was converted directly to the corresponding trifluoroborate salt by treatment with potassium bifluoride. Using this boronic acid method, (e.g. see Molander, G. A.; Trice, S. L. J.; Dreher, S. D. *J. Am Chem Soc.* 2010. 132, (50), 17701-17703) the yield of (9) increased to 93% over this two-step process, which results in an increased overall yield of telmisartan of 74%.

Experimental

Preparation of potassium (4-methyl-2-propyl-benzimidazole-6-yl) trifluoroborate (9)

6-bromo-4-methyl-2-propylbenzimidazole (14) (2.2 g, 8.7 mmol) was taken up in 80 mL of EtOH. The solution was added to a flask containing diboronic acid (2.3 g, 26.0 mmol), KOAc (2.5 g, 26.0 mmol), $PdCl_2(PPh_3)_2$ (182 mg, 0.26 mmol) and triphenylphosphine (91 mg, 0.35 mmol). The flask was then evacuated and placed under nitrogen. The solution was heated at 75° C. for 10 h. The reaction mixture was cooled, filtered and then concentrated by rotary evaporator followed by the addition of 80 mL of $H_2O$. The aqueous mixture was then extracted with EtOAc (3×100 mL). The organic layer was combined and concentrated to about 100 mL. The remaining solution was then combined with a solution of potassium bifluoride (3.4 g, 43.3 mmol) in $H_2O$. The biphasic mixture was stirred at room temperature for 5 hours. The precipitate was filtered, rinsed using THF and then dried, yielding 9 as a white solid (2.2 g, 90%). $^1H$ NMR (DMSO-$d_6$, 300 MHz) δ 7.38 (s, 1H), 7.27 (s, 1H), 3.03 (t, 2H), 2.50 (s, 3H), 1.86 (m, 2H), 0.96 (t, 3H); $^{13}C$ NMR (DMSO-$d_6$, 300 MHz) δ 151.8, 130.3, 130.0, 128.8, 120.8, 112.3, 27.9, 20.4, 16.6, 13.4; HRMS (ESI-QTOF): m/z Cald for $C_{11}H_{13}N_2BF_3K+H^+$: 281.0839, found 281.0819. While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

It is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

We claim:

1. A method of synthesizing telmisartan, comprising the step of coupling
    i) potassium(1-((2'-carboxy-[1,1'-biphenyl]-4-yl)methyl)-4-methyl-2-propyl-benzimidazole-6-yl) trifluoroborate and
    ii) 2-bromo-1-methylbenzimidazole,
wherein said step of coupling is carried out under Suzuki cross-coupling reaction conditions, to form said telmisartan.

2. The method of claim 1, wherein said step of coupling is carried out using microwave assisted heating.

3. The method of claim 1, further comprising the step of forming said potassium(1-((2'-carboxy-[1,1'-biphenyl]-4-yl)methyl)-4-methyl-2-propyl-benzimidazole-6-yl) trifluoroborate by
    i) pre-treating potassium(4-methyl-2-propyl-benzimidazole-6-yl) trifluoroborate with potassium tert-butoxide; and
    ii) alkylating pretreated potassium(4-methyl-2-propyl-benzimidazole-6-yl) trifluoroborate with methyl 4'-bromomethyl-biphenyl-2-carboxylate, to form said potassium(1-((2'-carboxy-[1,1'-biphenyl]-4-yl)methyl)-4-methyl-2-propyl-benzimidazole-6-yl) trifluoroborate.

4. The method of claim 1, further comprising the step of forming said 2-bromo-1-methylbenzimidazole by
regioselectively brominating a 2-position of 1-methylbenzimidazole to form 2-bromo-1-methylbenzimidazole.

5. The method of claim 3 further comprising the step of forming said potassium(4-methyl-2-propyl-benzimidazole-6-yl) trifluoroborate by
i) performing reductive cyclization of 4-bromo-2-methyl-6-nitroaniline in the presence of n-butyraldehyde and sodium dithionite to form 6-bromo-4-methyl-2-propylbenzimidazole; and
ii) converting said 6-bromo-4-methyl-2-propylbenzimidazole to a trifluoroborate salt, to form said potassium (4-methyl-2-propyl-benzimidazole-6-yl) trifluoroborate.

6. The method of claim 5, wherein said step of converting is performed by
reacting said 6-bromo-4-methyl-2-propylbenzimidazole with diboron pinacol ester in the presence of a catalyst to form a boronic acid pinacol ester; and
converting said boronic acid pinacol ester to said potassium(4-methyl-2-propyl-benzimidazole-6-yl) trifluoroborate.

7. The method of claim 6, wherein the catalyst is a Pd catalyst.

8. The method of claim 7, wherein the Pd catalyst is $PdCl_2dppf$.

9. The method of claim 5, wherein said step of converting is performed by
reacting said 6-bromo-4-methyl-2-propylbenzimidazole with diboronic acid in the presence of a catalyst to form 6-boronic acid-4-methyl-2-propylbenzimidazole; and
contacting said 6-boronic acid-4-methyl-2-propylbenzimidazole with $KHF_2$ to form said potassium(4-methyl-2-propyl-benzimidazole-6-yl) trifluoroborate.

10. The method of claim 9, wherein the catalyst is a Pd catalyst.

11. The method of claim 10, wherein the Pd catalyst is $PdCl_2(PPh_3)_2$.

12. The method of claim 1, wherein said step of coupling is catalyzed by a Pd catalyst.

13. The method of claim 12, wherein said Pd catalyst is a homogenous Pd catalyst.

14. The method of claim 13, wherein said homogenous Pd catalyst is $PdCl_2dppf$.

15. The method of claim 12, wherein said Pd catalyst is a heterogenous Pd catalyst.

16. The method of claim 15, wherein said heterogenous Pd catalyst is graphene supported Pd nanoparticles.

17. The method of claim 4, wherein said step of regioselectively brominating is performed by brominating a 2-position of 1-methylbenzimidazole by, in a solution with tetrahydrofuran (THF) as solvent, contacting an imidazole ring of said 1-methylbenzimidazole with a brominating agent, to form said 2-bromo-1-methylbenzimidazole.

18. The method of claim 17 wherein said brominating agent is N-bromosuccinimide.

* * * * *